(12) United States Patent
Le Portz

(10) Patent No.: US 9,308,067 B2
(45) Date of Patent: Apr. 12, 2016

(54) URETHRAL SUPPORT IMPLANT FOR THE TREATMENT OF MALE URINARY INCONTINENCE

(75) Inventor: Benoit Le Portz, Vannes (FR)

(73) Assignee: ASPIDE MEDICAL, La Talaudiere (FR)

( * ) Notice: Subject to any disclaimer, the term of this patent is extended or adjusted under 35 U.S.C. 154(b) by 416 days.

(21) Appl. No.: 13/642,575

(22) PCT Filed: Apr. 22, 2011

(86) PCT No.: PCT/FR2011/050936
§ 371 (c)(1),
(2), (4) Date: Nov. 12, 2012

(87) PCT Pub. No.: WO2011/131916
PCT Pub. Date: Oct. 27, 2011

(65) Prior Publication Data
US 2013/0061727 A1    Mar. 14, 2013

(30) Foreign Application Priority Data
Apr. 23, 2010 (FR) ...................................... 10 53091

(51) Int. Cl.
*A61F 2/00* (2006.01)
*B26D 3/00* (2006.01)

(52) U.S. Cl.
CPC ................ *A61F 2/0045* (2013.01); *B26D 3/00* (2013.01); *A61F 2250/006* (2013.01); *Y10T 83/04* (2015.04)

(58) Field of Classification Search
CPC ....... A61F 2/00; A61F 2/0004; A61F 2/0031; A61F 2/0036; A61F 2/0045; A61F 2/0063; A61F 2/0077; A61F 2250/006; D04B 21/10; D04B 21/20; D10B 2509/08

USPC .............. 600/29–31, 37; 606/151; 623/23.66, 623/23.72
See application file for complete search history.

(56) References Cited

U.S. PATENT DOCUMENTS 6,290,708 B1 * 9/2001 Kugel ................... A61F 2/0063
602/44
7,407,480 B2    8/2008 Staskin et al.
(Continued)

FOREIGN PATENT DOCUMENTS

FR    2906131 A1    3/2008
FR    2926455 A1    7/2009
(Continued)

OTHER PUBLICATIONS

International Search Report for PCT/FR2011/050936 dated Jul. 29, 2011.

*Primary Examiner* — Charles A Marmor, II
*Assistant Examiner* — Carrie R Dorna
(74) *Attorney, Agent, or Firm* — Heslin Rothenberg Farley & Mesiti P.C.

(57) ABSTRACT

A urethral support sling implant for treatment of male urinary incontinence is produced in a biocompatible material and comprises a central part intended to form the area supporting the urethra, including an inferior base prolonged into two trans-obturator arms in the same plane and in opposition to each other. The inferior base is prolonged upwards by a section extending beyond the inferior base in the form of two pre-pubic arms. The prolonging arms are made of the same material as the central part, and the arms are produced in the same direction of knit. The pre-pubic arms are configured in a 'V' relative to each other, and each of the pre-pubic arms is configured in a 'V' relative to the subjacent trans-obturator arm.

3 Claims, 6 Drawing Sheets

(56) References Cited

U.S. PATENT DOCUMENTS

| | | |
|---|---|---|
| 7,431,690 B2 | 10/2008 | Merade et al. |
| 7,559,885 B2 | 7/2009 | Merade et al. |
| 2004/0039453 A1 | 2/2004 | Anderson et al. |
| 2005/0070829 A1* | 3/2005 | Therin et al. ................. 602/1 |
| 2006/0122457 A1* | 6/2006 | Kovac ................. A61F 2/0036 600/37 |
| 2008/0177132 A1* | 7/2008 | Alinsod ................. A61F 2/0045 600/37 |

FOREIGN PATENT DOCUMENTS

| | | |
|---|---|---|
| FR | 2934150 A1 | 1/2010 |
| WO | 2007149348 A2 | 12/2007 |
| WO | 2009086369 A2 | 7/2009 |
| WO | 2009086446 A1 | 7/2009 |

* cited by examiner

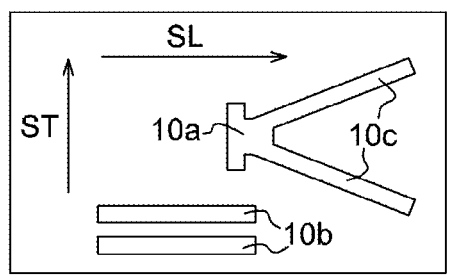
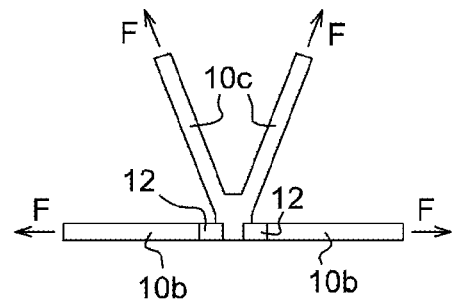
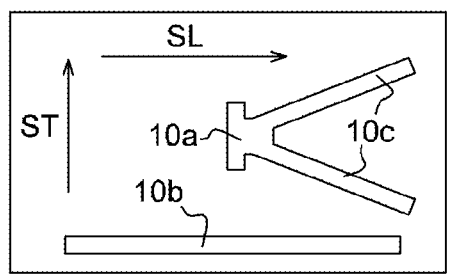
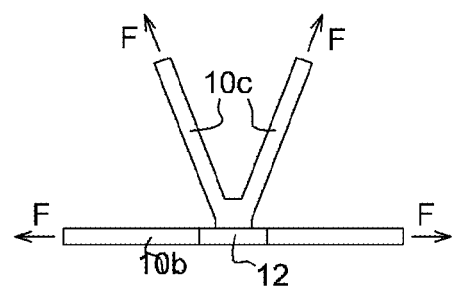
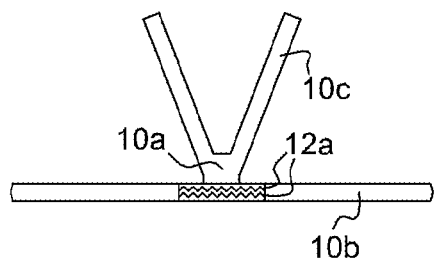
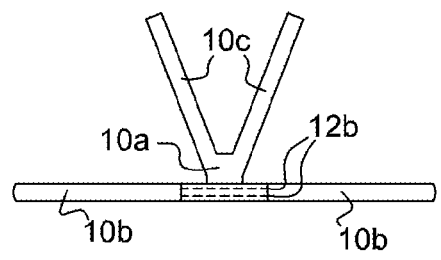
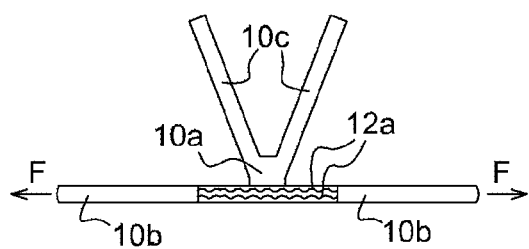
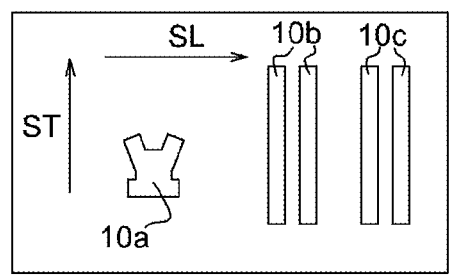

URETHRAL SUPPORT IMPLANT FOR THE TREATMENT OF MALE URINARY INCONTINENCE

CROSS REFERENCE TO RELATED APPLICATIONS

This application is a national stage filing under section 371 of International Application No. PCT/FR2011/050936 filed on Apr. 22, 2011, and published in French on Oct. 27, 2011 as WO 2011/131916 A1 and claims priority of French application No. 1053091 filed on Apr. 23, 2010, the entire disclosure of these applications being hereby incorporated herein by reference.

BACKGROUND ART

The invention falls within the technical field of implants for the treatment of male urinary incontinence. This incontinence can result from prostatectomy performed to treat prostate cancer.

More generally, there exist implants or devices to treat this incontinence, the majority of which make use of the principle of the sub-urethral sling, widely known for the treatment of urinary stress incontinence in women.

Many implants or devices have been described for treating male or female incontinence. For example, the applicant has developed solutions described in the French patents 2934150 and 2926455. Others have also published patents such as FR 2906131, U.S. Pat. Nos. 7,431,690, 7,559,885, EP 2025304.

Figure 1:
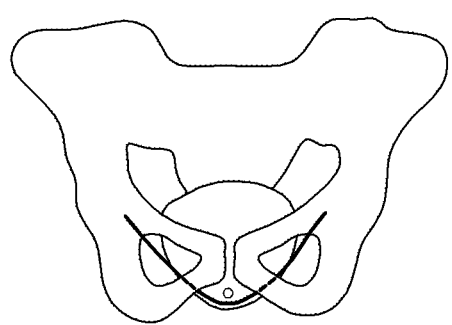
Figure 2:
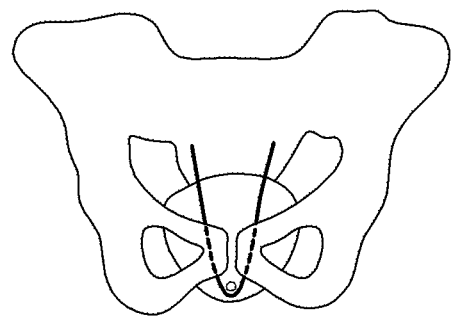

For the treatment of female urinary incontinence the main solutions used insert the sling through the obturator foramina of the pelvis following a trans-obturator route. It has also been proposed that the sling should be inserted posterior to the pubis via the retro-pubic route. FIGS. 1 and 2 show diagrams of the route taken by the sling in these two situations.

For mild to moderate male urinary incontinence, the devices are mainly based on the trans-obturator route.

The applicant has observed that the efficacy of these devices or implants was still poor. Prior art solutions provide localized support for the urethra, but this can lead to migration of the sling or limited efficacy.

From the documents U.S. 2004/039453 and WO 2009/086446 we know, moreover, of implants the constituent parts of which have characteristics and mechanical properties that can vary because of different weaving/knitting processes.

The applicant's approach lay therefore in reconsidering the design of the implant to allow the urethra to be held more securely, limit the risk of sling migration and to optimize the device. In view of the prior art, the solution provided by the applicant is simple in design and answers the problem posed to advantage.

BRIEF SUMMARY OF THE INVENTION

According to a first characteristic, the urethral support implant for the treatment of male urinary incontinence is a type of sling in a biocompatible material comprising a central part intended to form the area supporting the urethra, consisting of an inferior base which is prolonged into two trans-obturator arms (in the same plane and in opposition to each other), the inferior base being prolonged upwards by a section extending beyond the said inferior base, this also prolonged in the form of two pre-pubic arms. The remarkable features of these two prolonging arms are that they are made in the same material as the central part, the said arms are produced in the same direction of knit, the said pre-pubic arms are configured in a 'V' relative to each other, and each of the said pre-pubic arms is configured in a 'V' relative to the subjacent trans-obturator arm.

These characteristics and many others too will become evident in the rest of the description.

BRIEF DESCRIPTION OF THE DRAWING FIGURES

Figure 3A:
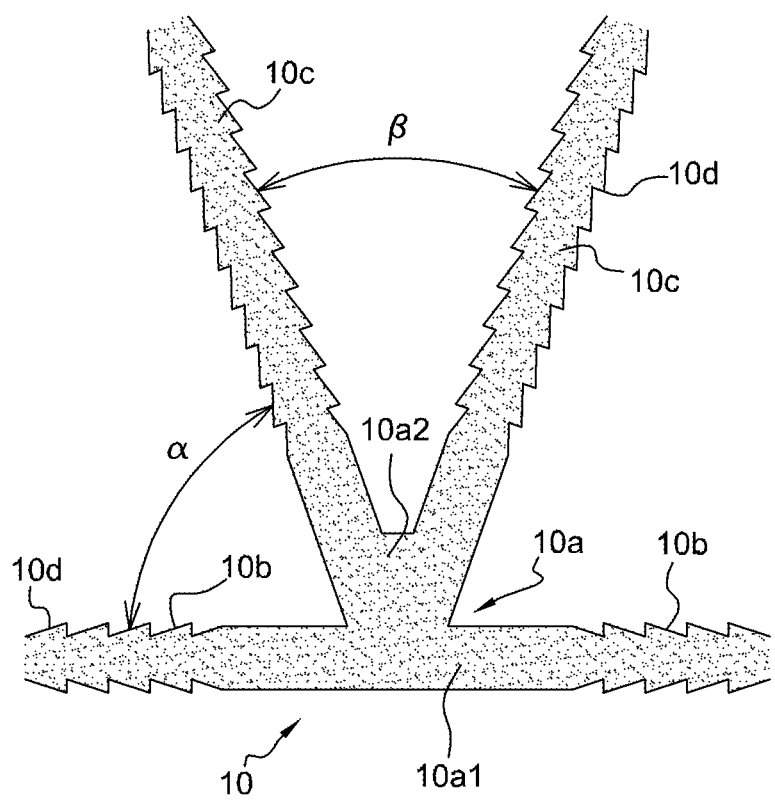
Figure 3B:
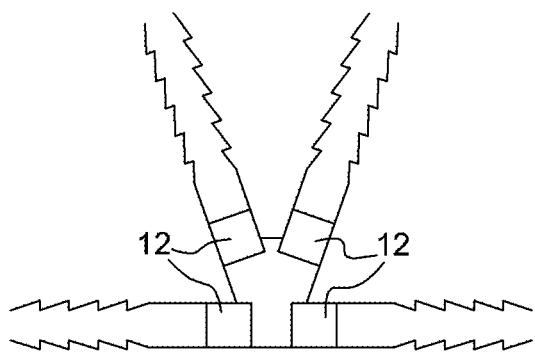
Figure 3C:
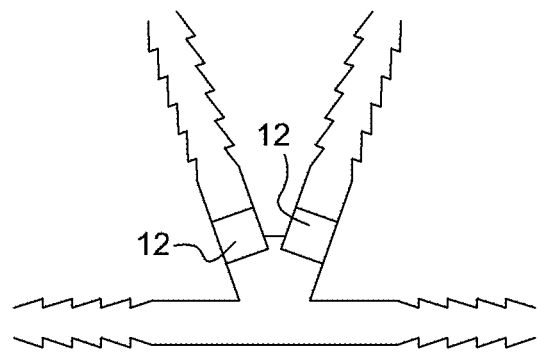
Figure 3D:
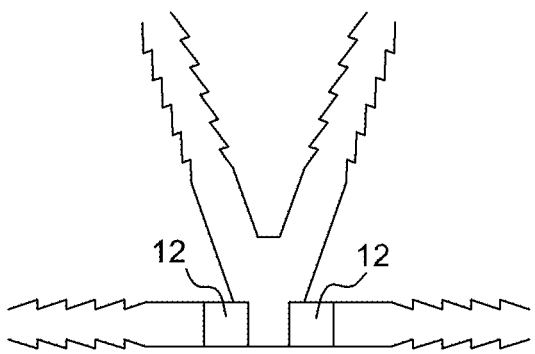
Figure 3E:
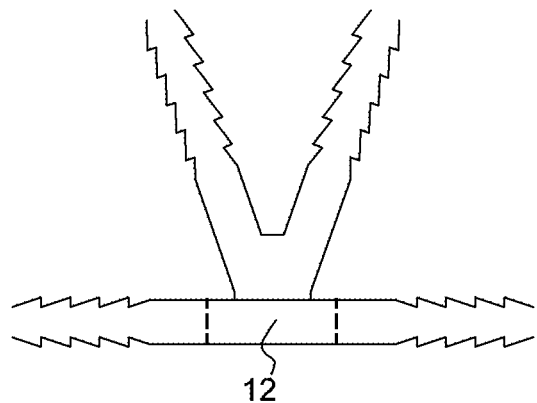
Figure 4:
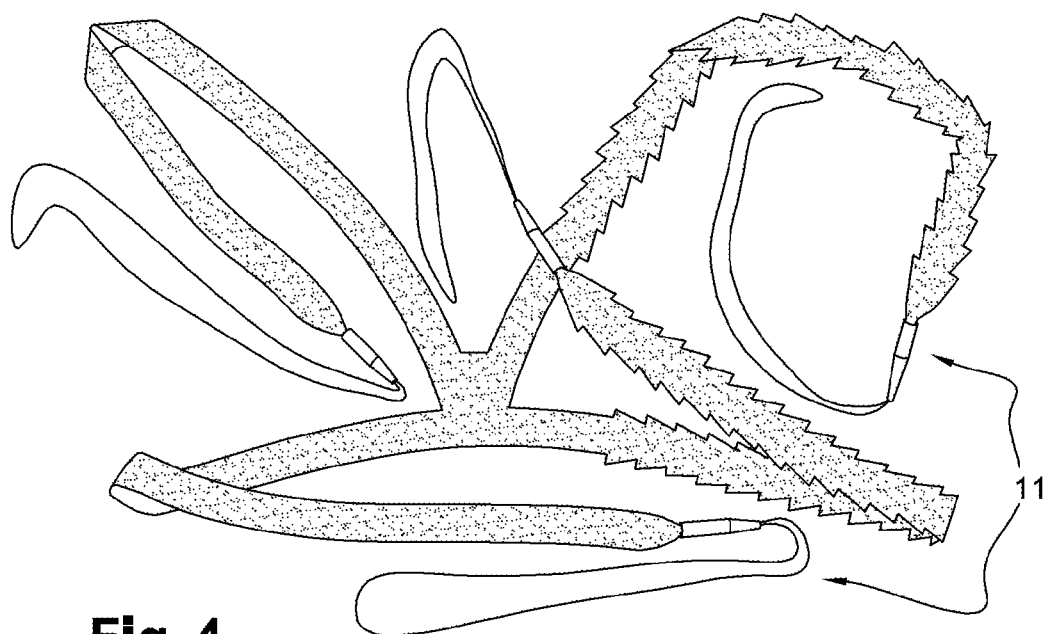
Figure 5:
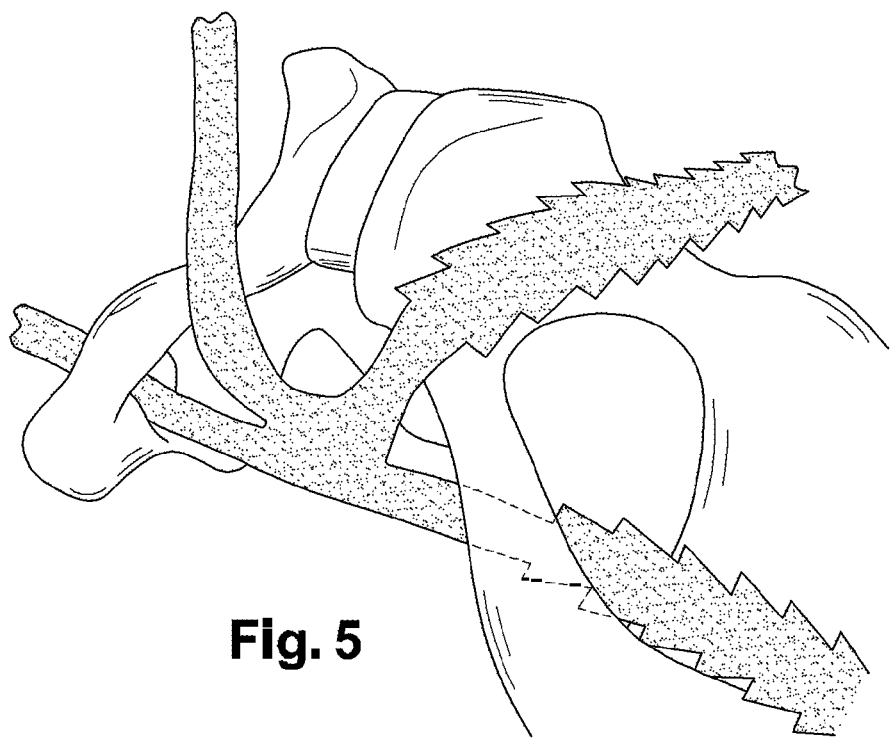
Figure 6:
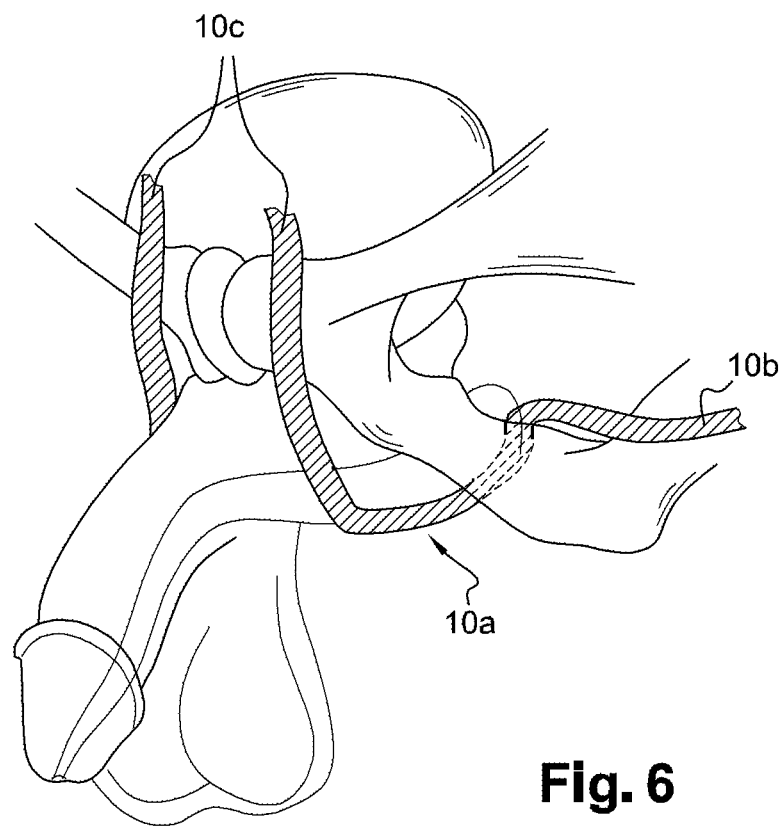
Figure 7:
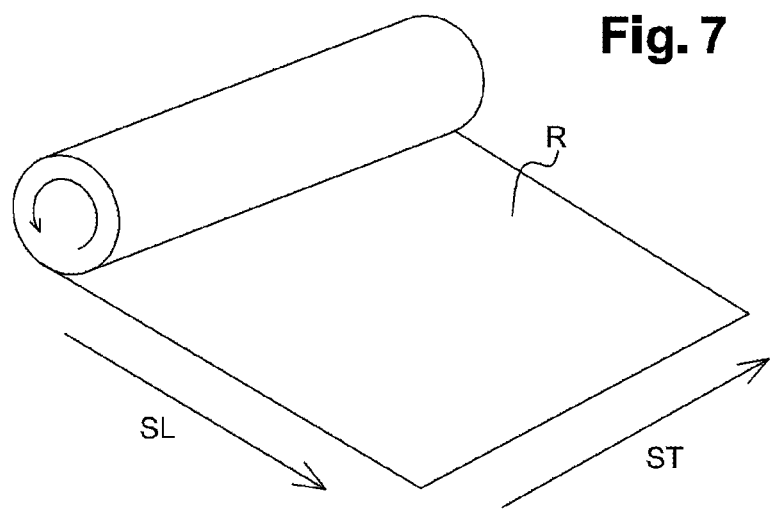
Figure 8A:
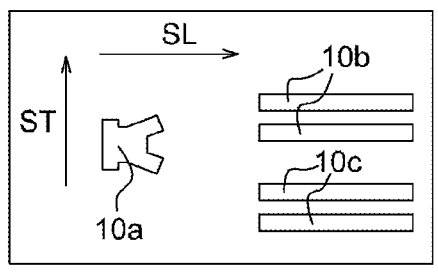
Figure 8B:
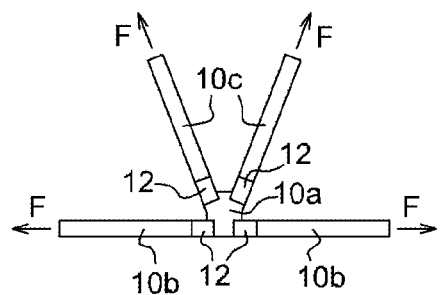
Figure 9A:
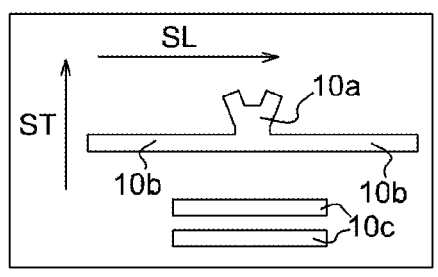
Figure 9B:
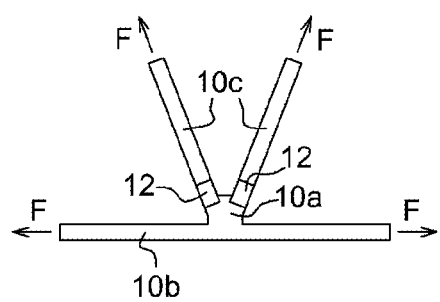

To make the object of the invention clear, it is shown in a non-limiting manner in the accompanying drawings, where FIGS. 1 and 2 are diagrams illustrating the implants used for female incontinence in the form of a sling and positioned relative to the pelvis with a trans-obturator and a retro-pubic pathway, respectively, FIGS. 3A, 3B, 3C, 3D, 3E are diagrams illustrating the urethral support implant according to the invention, FIG. 4 is an overall view of a support implant according to the invention, FIG. 5 is a view illustrating how the support implant according to the invention is fitted and its path and position relative to the pelvis, FIG. 6 is a diagram of the support implant according to the invention placed in position, FIG. 7 is a diagram illustrating a roll of knitted fabric from which the implant is manufactured in an optimized version of the invention, FIG. 8A is a flat diagram illustrating, in a first variant of the optimized version, cutting the trans-obturator and pre-pubic arms, and also the central part, in the longitudinal direction of the knit, FIG. 8B is a flat view of the implant assembled as cut out according to FIG. 8A, FIG. 9A is a flat diagram illustrating, in a second variant of the optimized version, cutting the trans-obturator arms as a single piece with the central part and cutting the independent pre-pubic arms in the longitudinal direction of the knit, FIG. 9B is a flat view of the implant assembled as cut out according to FIG. 9A, FIG. 10A is a flat diagram illustrating a third variant in the optimized version in which the pre-pubic arms are cut as a single piece with the central part and the trans-obturator arms are cut in the longitudinal direction of the knit, FIG. 10B is a flat view of the implant assembled as cut out according to FIG. 10A, FIG. 11A is a flat diagram illustrating the pre-pubic arms cut as a single piece with the central part and the trans-obturator arms cut as a single piece in the longitudinal direction of the knit, FIG. 11B is a flat view of the implant assembled as cut out according to FIG. 11A, FIG. 12 is a view of a cutting variant in which the components, e.g. those of FIG. 8A, are cut out in the transverse direction of the knit, FIGS. 13A and 13B are diagrams illustrating the ways of assembling the trans-obturator arms sewing them respectively with a zigzag and straight stitch, with no strain applied, FIG. 13C is a view of the implant according to FIG. 13A with traction applied to the trans-obturator arms.

DETAILED DESCRIPTION

In order to make the object of the invention clearer, it will now be described in a non-exhaustive manner illustrated by the drawings in the figures.

With reference to FIGS. 3 to 13C, the urethral support implant for the treatment of male urinary incontinence is of the type made as a knitted, braided or other form of sling in a polypropylene or similar biocompatible material to be fitted under the patient's urethra. It is produced from a roll (R) of knitted material suitable for this application.

According to the invention, the implant (10) in the form of a sling comprises a central part (10a) intended to form the area supporting the urethra. This central part has an inferior base (10a1) which may be prolonged to allow two opposite trans-obturator arms (10b) to be fixed and joined to it in the same plane. The length of these arms is calculated depending on the anatomy of the male pelvis. The inferior base (10a1) is prolonged upwards by a section (10a2) extending from the said inferior base to which are attached and fixed two pre-pubic arms (10c). The latter are configured one with the other in a 'V', the angle of which take into account the morphology of the pelvis. This angle β is in the order of 30 to 50°. Moreover each of the said pre-pubic arms (10C) is also configured in a 'V' relative to the subjacent trans-obturator arm (10B) with an angle α in the order of 60 to 80°.

The implant thus produced can be a single unit cut in one piece from the same material (FIG. 3A) or the arms (10b)-(10c) may to advantage be joined to the central part by any appropriate means and particularly by welding, sewing or other method (FIGS. 3B, 3C, 3D, 3E) in order to optimize their mechanical characteristics, particularly elongation, and choose the best direction of the knit forming each arm (10b)-(10c).

In a variant, at least one of the prolonging arms (10b) (10c) is produced as a single unit with the central part (10a) and at least one of the prolonging arms (10b) (10c) is produced independently and joined to the central part (10a) by any means.

In a variant, several prolonging arms (10b) (10c) are joined and linked to the central part (10a) by any means (FIG. 3E).

In an optimized embodiment, the prolonging arms (10b-10c) are made in the same material as the central part (10a).

In this optimized embodiment, consideration is given to the roll of knitted fabric (R) that is used to cut out the various parts forming the implant so as to have and obtain the said pre-pubic and trans-obturator arms cut in the strongest direction of the knit.

This roll unrolls in a given direction, the longitudinal direction (SL) being defined as this direction in which the knitted fabric unrolls, and the transverse direction (ST) being the direction that is perpendicular to the longitudinal direction (FIG. 7). The knitted fabric thus has one direction which is mechanically stronger than the other and one direction with a greater capacity for stretching than the other. The properties can thus be established according to FIGS. 8A to 11B where the longitudinal direction has the property of being mechanically stronger and the transverse direction of stretching more. Conversely, in FIG. 12, the transverse direction is mechanically stronger and the longitudinal direction more extensible (this depending on the way that the knitted fabric is made). The essential point according to the invention is that the trans-obturator and pre-pubic arms should all be cut in the same direction. In order to optimize making the implant and particularly the mechanical behavior of its arms, the invention consists of cutting out each part of the implant and therefore the arms in the most favorable direction and orientation of the knit in terms of mechanical behavior (maximum mechanical strength and minimum stretch). The parts are then assembled to form the final implant.

Referring to FIGS. 8A and 8B, the four trans-obturator (10b) and pre-pubic (10c) arms are all cut in the longitudinal direction, and the central part is cut in such a way that the parts of it which join the pre-pubic arms are oriented in the longitudinal direction of the knit. The parts of the assembly are identified by (12).

Referring to FIGS. 9A-9B, the trans-obturator arms (10b) forming a single unit with the central part (10a) and also the pre-pubic arms (10c) are cut in the longitudinal direction of the knit. The parts of the assembly are identified by (12).

Referring to FIGS. 10A-10B, the pre-pubic arms (10c) and the central part (10a) are cut out as a single unit, whereas the trans-obturator arms (10b) are independent. The pre-pubic arms are oriented in the longitudinal direction of the knit but at an angle while still largely retaining the properties of the knit in the longitudinal direction. The parts of the assembly are identified by (12).

Referring to FIGS. 11A-11B, the pre-pubic arms (10c) form a single unit with the central part (10a) and the trans-obturator arms (10b) form a single unit cut from the knitted fabric. The pre-pubic arms are oriented in the longitudinal direction of the knit but at an angle while still largely retaining the properties of the knit in the longitudinal direction. The trans-obturator arms are oriented in the longitudinal direction of the knit.

FIG. 12 shows a diagram for cutting out the various components as described in FIGS. 8A to 11A in the transverse direction of the knitted fabric to optimize the characteristics of each arm (10b-10c) depending on the knit of the roll of fabric to be cut. Obviously, the various cutting variants in FIGS. 8A to 11A can be applied to cutting in the transverse direction of the knit.

The cutting solutions thus used mean that each arm (10b-10c) can be cut out in the most favorable direction of the fabric depending on the orientation of the knit of the fabric, and that therefore the mechanical characteristics of each arm (maximum mechanical strength and minimum elongation when the arms are subjected to a traction force (F)) can be optimized and homogeneity obtained.

In addition, depending on the cutting variants, the number of components to be cut out and assembled can be limited by optimizing production.

If a single unit with continuous trans-obturator arms (10b) is used a still stronger assembly can be expected.

Each arm is joined to the central part by any appropriate means, the central part in all cases having a starting point for configuring and positioning the arms.

As illustrated in a non-exhaustive manner in the drawings, the arm or arms may be shaped as harpoons (10d) or notches which could form anchorage points limiting the arms slipping in the tissues. At the ends of the said arms there may be loops (11) or shaped ends or any other means of grasping them to assist their insertion.

Another advantageous embodiment of the invention in FIGS. 13A to 13C shows an implant in two assembled parts consisting of a single unit with pre-pubic arms (10c) and a central part (10a) and another single unit forming the trans-obturator arms (10b) in a continuous single strip.

They are assembled and joined using zigzag stitching (12a), FIG. 13A, or straight stitching (12b), FIG. 13B.

The advantage of zigzag stitching as it appears in FIG. 13C is that it can more easily absorb the deformations and mechanical strains when the trans-obturator arms are put under tension, without risk of the sewing thread breaking prematurely.

According to the invention the implant produced thus provides dual stability, trans-obturator on the one hand and pre-pubic on the other. The pairs of arms are fitted in a known way using suitable instruments for inserting each one. The central part of the implant according to the invention provides a very large area of support for the urethra which is thus held supported by the four previously mentioned arms, thus treating male urinary incontinence effectively.

According to the invention, the central part and the four arms are made and cut from the same material with the same knit. Cutting the four arms in the same longitudinal or transverse direction of the knitted fabric and with the same optimal mechanical properties both optimizes the mechanical and elongation properties of the arms and their orientation to create effective trans-obturator and pre-pubic arms.

The invention is thus remarkable due to the process thus defined for cutting out all the components of the implant in a knitted fabric in a longitudinal or transverse direction with a view to having the same mechanical properties for the arms to ensure homogeneity and optimization of use of the implant. Knitted fabric, which has two directions, longitudinal and transverse, always has one direction stronger than the other, and the particularity of the invention is in cutting out the arms (10b) (10c) in the direction which is mechanically stronger.

The invention claimed is:

1. Manufacturing process for a urethral support sling implant for treatment of male urinary incontinence, produced in a biocompatible material, comprising a central part forming an area adapted for supporting the urethra, including an inferior base prolonged in a same plane by two opposite trans-obturator arms, the inferior base being prolonged upwards by a section extending beyond said inferior base, the section also extending as two pre-pubic arms configured in a 'V' relative to each other, and each of said pre-pubic arms being configured in a 'V' at an angle greater than 45° relative to subjacent trans-obturator arms, the trans-obturator arms and the pre-pubic arms being made of a same material as the central part, wherein the process comprises: cutting the pre-pubic arms, the trans-obturator arms and the central part from a knitted fabric having a first direction, and a second direction, transverse to the first direction, the first direction being of higher mechanical strength than the second direction, the second direction being of higher extensibility than the first direction, cutting said trans-obturator arms as a single continuous strip extending in the first direction from the knitted fabric, cutting the pre-pubic arms and the central part out of the knitted fabric as a single unit, separate from the trans-obturator arms, and with the pre-pubic arms extending primarily in the first direction, and assembling the trans-obturator arms to the central part with zig-zag stitching of sewing thread to absorb deformations and mechanical strains when the trans-obturator arms are put under tension, without risk of the sewing thread breaking prematurely.

2. The manufacturing process according to claim 1, wherein the angle greater than 45° comprises an angle between 60° and 80°.

3. The manufacturing process according to claim 1, further comprising shaping at least some of the trans-obturator arms and the pre-pubic arms as harpoons or notches for anchorage in tissue.

* * * * *